United States Patent [19]

Forbus

[11] Patent Number: 5,026,948
[45] Date of Patent: Jun. 25, 1991

[54] DISPROPORTIONATION OF ALPHA-OLEFIN DIMER TO LIQUID LUBRICANT BASESTOCK

[75] Inventor: Thomas R. Forbus, Newton, Pa.

[73] Assignee: Mobil Oil Corporation, Fairfax, Va.

[21] Appl. No.: 313,401

[22] Filed: Feb. 21, 1989

[51] Int. Cl.$^5$ .......................... C07C 2/10; C07C 6/02
[52] U.S. Cl. .................................. 585/646; 585/324; 585/329
[58] Field of Search ............... 585/510, 530, 646, 324, 585/329

[56] References Cited

U.S. PATENT DOCUMENTS

| | | | |
|---|---|---|---|
| 3,442,964 | 5/1969 | Oldhem | 585/464 |
| 3,637,503 | 1/1972 | Gianetti | |
| 3,795,616 | 3/1974 | Heilman et al. | |
| 4,180,524 | 12/1979 | Reussen et al. | 585/646 |
| 4,247,421 | 1/1981 | McDaniel et al. | |
| 4,282,392 | 8/1981 | Cupples et al. | |
| 4,363,342 | 1/1983 | Slaugh | 585/457 |
| 4,368,141 | 1/1983 | Kukes | 585/646 |
| 4,547,617 | 10/1985 | Welch | 585/646 |
| 4,587,368 | 5/1986 | Pratt | |
| 4,605,810 | 8/1986 | Banks | 585/646 |
| 4,609,769 | 9/1986 | Kukes et al. | 585/646 |
| 4,665,245 | 5/1987 | Quann | 585/646 |
| 4,827,064 | 5/1989 | Wu | 585/10 |
| 4,827,073 | 5/1989 | Wu | 585/530 |
| 4,912,277 | 3/1990 | Aufdembrink et al. | 585/467 |
| 4,914,254 | 4/1990 | Pelrine | 585/530 |

FOREIGN PATENT DOCUMENTS

| | | | |
|---|---|---|---|
| 3427319 | 1/1986 | Fed. Rep. of Germany | 585/530 |
| 2414542 | 1/1978 | France | 585/456 |

Primary Examiner—Asok Pal
Attorney, Agent, or Firm—Alexander J. McKillop; Charles J. Speciale; Malcolm D. Keen

[57] ABSTRACT

A process is disclosed for the preparation of low viscosity lubricant range hydrocarbons having high viscosity index which comprises: contacting olefinic dimer, or mixtures thereof, with a Group 6 metal oxide disproportionation catalyst on a solid support under disproportionation reaction conditions. The dimer comprises the product of the oligomerization of $C_6$–$C_{20}$ alpha-olefins in contact with reduced chromium oxide catalyst on silica support. The disproportionation catalyst preparation includes treatment by oxidation at a temperature of 200° C. to 900° C. in the presence of an oxidizing gas and then treatment with a reducing agent at a temperature and a time sufficient to reduce said catalyst. The disproportionation reaction effluent is separated and lubricant range hydrocarbons recovered. The preferred disproportionation catalyst for the process is reduced tungsten oxide on silica support.

9 Claims, 2 Drawing Sheets

1

CIS & TRANS - 2

CIS & TRANS - 3

4

CIS & TRANS - 5

CIS & TRANS - 6

DISPROPORTIONATION OF ALPHA-OLEFIN DIMER TO LIQUID LUBRICANT BASESTOCK

This invention relates to a novel process and compositions therefrom for the conversion of olefinic hydrocarbons of non-lubricant range molecular weight to low viscosity synthetic liquid hydrocarbon lubricants. The invention particularly relates to the conversion of non-lube range oligomeric alkene hydrocarbons containing exo-olefin groups to higher molecular weight lube range alkenes. More particularly, the invention relates to the production of higher molecular weight liquid lubricant hydrocarbons by catalytic disproportionation of alpha-olefin dimers produced in the course of the oligomerization of $C_6$–$C_{20}$ alpha-olefins.

BACKGROUND OF THE INVENTION

Efforts to improve upon the performance of natural mineral oil based lubricants by the synthesis of oligomeric hydrocarbon fluids have been the subject of important research and development in the petroleum industry for at least fifty years and have led to the relatively recent market introduction of a number of superior polyalpha-olefin ((PAO) synthetic lubricants, primarily based on the oligomerization of alpha-olefins or 1-alkenes. In terms of lubricant property improvement, the thrust of the industrial research effort on synthetic lubricants has been toward fluids exhibiting useful viscosities over a wide range of temperature, i.e., improved viscosity index (VI), while also showing lubricity, thermal and oxidative stability and pour point equal to or better than mineral oil. These new synthetic lubricants lower friction and hence increase mechanical efficiency across the full spectrum of mechanical loads from worm gears to steel gears and do so over a wider range of operating conditions than mineral oil lubricants.

Recently, novel lubricant compositions (referred to herein as HVI-PAO and the HVI-PAO process) comprising polyalpha-olefins and methods for their preparation employing as catalyst reduced chromium on a silica support have been disclosed in U.S. patent applications Ser. Nos. 210,434 and 210,435 filed June 23, 1988, now U.S. Pat. Nos. 4,827,064 and 4,827,073, incorporated herein by reference in their entirety The process comprises contacting $C_6$–$C_{20}$ 1-alkene feedstock with reduced valence state chromium oxide catalyst on porous silica support under oligomerizing conditions in an oligomerization zone whereby high viscosity, high VI liquid hydrocarbon lubricant is produced having branch ratios, i.e. $CH_3/CH_2$, less than 0.19 and pour point below $-15°$ C. The process is distinctive in that little isomerization of the olefinic bond occurs compared to known oligomerization methods to produce polyalpha-olefins using Lewis acid catalyst. Lubricants produced by the process cover the full range of lubricant viscosities and exhibit a remarkably high viscosity index (VI) and low pour point even at high viscosity. The as-synthesized HVI-PAO oligomer has a preponderance of terminal olefinic unsaturation, or exo-olefinic groups.

In the preparation of the novel HVI-PAO lubricant, alpha-olefin dimer containing olefinic unsaturation can be separated from the oligomerization reaction. The composition of the dimer mixture conforms to the unique specificity of the oligomerization reaction in that little double bond isomerization is found. Separation of the dimer, representing non-lube range molecular weight material, is necessitated to control product volatility and viscosity. However, as oligomerization conditions are changed to produce the lower viscosity products of lower average molecular weight important to the marketplace, the non-lube range dimer fraction by-product yield increases in proportion to that lowering in average molecular weight of the oligomerization product. In the synthesis of low average molecular weight oligomers substantial amounts of products stop at the dimer stage. Once so formed, they are inert to the further incorporation of olefin in the HVI-PAO oligomerization reaction. The increase in dimer by-product yield represents a substantial economic burden on the overall process to produce useful lower viscosity lubricant in the HVI-PAO process.

Accordingly, it is an object of the present invention to provide a process for the conversion of alkenes containing exo-olefin groups to higher molecular weight lube range hydrocarbons.

It is another object of the present invention to provide a process for the utilization of the HVI-PAO process by-product dimer for the further production of synthetic lubricant fluid.

It is another object of the present invention to provide a process for the production of low viscosity lubricant exhibiting superior lubricant properties utilizing HVI-PAO dimer.

Yet another object of the instant invention is to provide novel lubricant compositions that display superior lubricant properties derived from alpha-olefin dimers.

SUMMARY OF THE INVENTION

The discovery has been made that the mono-olefinic dimers produced in the course of the oligomerization of alpha-olefins can be converted to lighter and heavier olefins by disproportionation in a process known as metathesis. It has been found that the product of the reaction represents a bimolecular adduct of the dimer and produces a hydrocarbon disproportionation product useful as a lubricant plus an olefin by-product. Surprisingly, the hydrocarbon product displays a high viscosity index and low viscosity.

More particularly, a process has been discovered for the preparation of low viscosity lubricant range hydrocarbons having high viscosity index which comprises:- contacting olefinic dimer, or mixtures thereof, with a Group 6 metal oxide disproportionation catalyst on a solid support under disproportionation reaction conditions, said dimer comprising the product of the oligomerization of $C_6$–$C_{20}$ alpha-olefins in contact with reduced chromium oxide catalyst on silica support. The disproportionation catalyst preparation includes treatment by oxidation at a temperature of 200° C. to 900° C. in the presence of an oxidizing gas and then treatment with a reducing agent at a temperature and a time sufficient to reduce said catalyst. The disproportionation reaction effluent is separated and lubricant range hydrocarbons recovered. The preferred disproportionation catalyst for the process is reduced tungsten oxide on silica support.

The invention comprises a process for the conversion of non-lube range alkene oligomers containing exo-olefin groups to higher molecular weight lube range alkenes, comprising;

contacting said non-lube range alkene oligomers with Group 6 metal oxide catalyst under conditions sufficient to effect a bimolecular conversion of said non-lube alkene oligomers to an equal number of moles of lube range alkene oligomer and non-lube range alkene.

It has been found that the instant invention produces a novel lubricant composition which comprises the mono-olefinic bimolecular adduct of $C_{12}$–$C_{40}$ mono-olefin hydrocarbons. The adduct contains between $2n-2$ and $2n-(n/2+3)$ carbon atoms, where n is the number of carbon atoms in said $C_{12}$–$C_{40}$ mono-olefins hydrocarbons. A preferred mono-olefin hydrocarbon comprises $C_{20}$ mono-olefins.

DETAILED DESCRIPTION OF THE INVENTION

In the preferred embodiments of the present invention synthetic hydrocarbon lubricants are prepared from unique olefin dimers produced as by-product in the HVI-PAO oligomerization reaction. When alpha-olefin, such as 1-decene, is oligomerized in the HVI-PAO process products with very high viscosity indices and low pour points are obtained. Retention of the low pour point properties of these oligomers upon hydrogenation, a necessary process to impart good oxidative stability to these products, requires reduction of the dimers to very low levels. In the synthesis of low viscosity fluids by this process a substantial amount of the 1-decene is dimer. This limits the yield of lube range product and gives a substantial amount of by-product which adversely effects overall process economics. The dimers are separated from the oligomerization reaction product typically by distillation inorder to meet lube specifications such as volatility, viscosity and pour point.

The HVI-PAO process consists of the oligomerization of 1-alkenes in contact with reduced chromium oxide on silica support. A characteristic of the novel oligomerization reaction from which the by-product dimers used in the present invention are produced is the production of mixtures of dialkyl vinylidenic and 1,2 dialkyl or trialkyl mono-olefin oligomers, or HVI-PAO oligomers, as determined by infra-red and NMR analysis. However, in general, the HVI-PAO oligomers have the following regular head-to-tail structure where n is preferably 0 to 17, terminating in olefinic unsaturation:

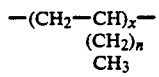

with some head-to-head connections.

The HVI-PAO process produces a surprisingly simpler and useful dimer compared to the dimer produced by 1-alkene oligomerization with $BF_3$ or $AlCl_3$ as commercially practiced. Typically, in the present invention it has been found that a significant proportion of unhydrogenated dimerized 1-alkene, or alpha-olefin, has a vinylidenyl structure as follows:

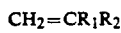

where $R_1$ and $R_2$ are alkyl groups representing the residue from the head-to-tail addition of 1-alkene molecules. For example, the by-product dimer from 1-decene oligomerization according to the HVI-PAO process, which can be used as the mono-olefin feedstock in the present invention, has been found to contain three major components, as determined by GC. Based on C-13 NMR analysis, the unhydrogenated components were found to be 8-eicosene, 9-eicosene, 2-octyldodecene and 9-methyl-8 or 9-methyl-9-nonadecene.

Figure 1:
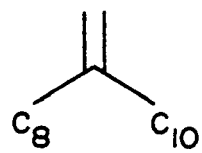
FIG. 1 illustrates the possible dimer structures from the oligomerization of 1-decene according to the HVI-PAO process.
Figure 1:
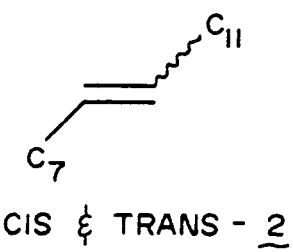
Figure 1:
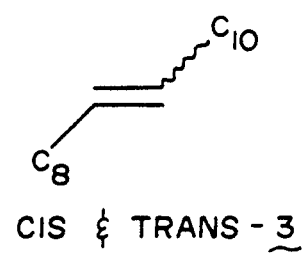
Figure 1:
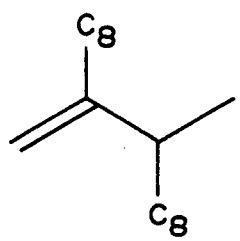
Figure 1:
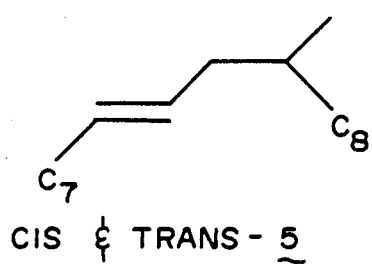
Figure 1:
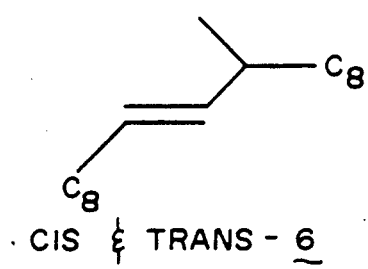

The dimers that are obtainable from 1-decene oligomerization, for example, by the HVI-PAO process are four general structure isomers in which two internal olefin products have a pair of double bond positional isomers plus cis/trans configurations. This gives ten possible dimer structures from 1-decene which are shown in FIG. 1. From analysis of the product mixture of hydrogenated dimer, structures 1, 2 and 3, shown in FIG. 1, are the major dimer products produced from 1-decene oligomerization with the HVI-PAO process.

Figure 2:
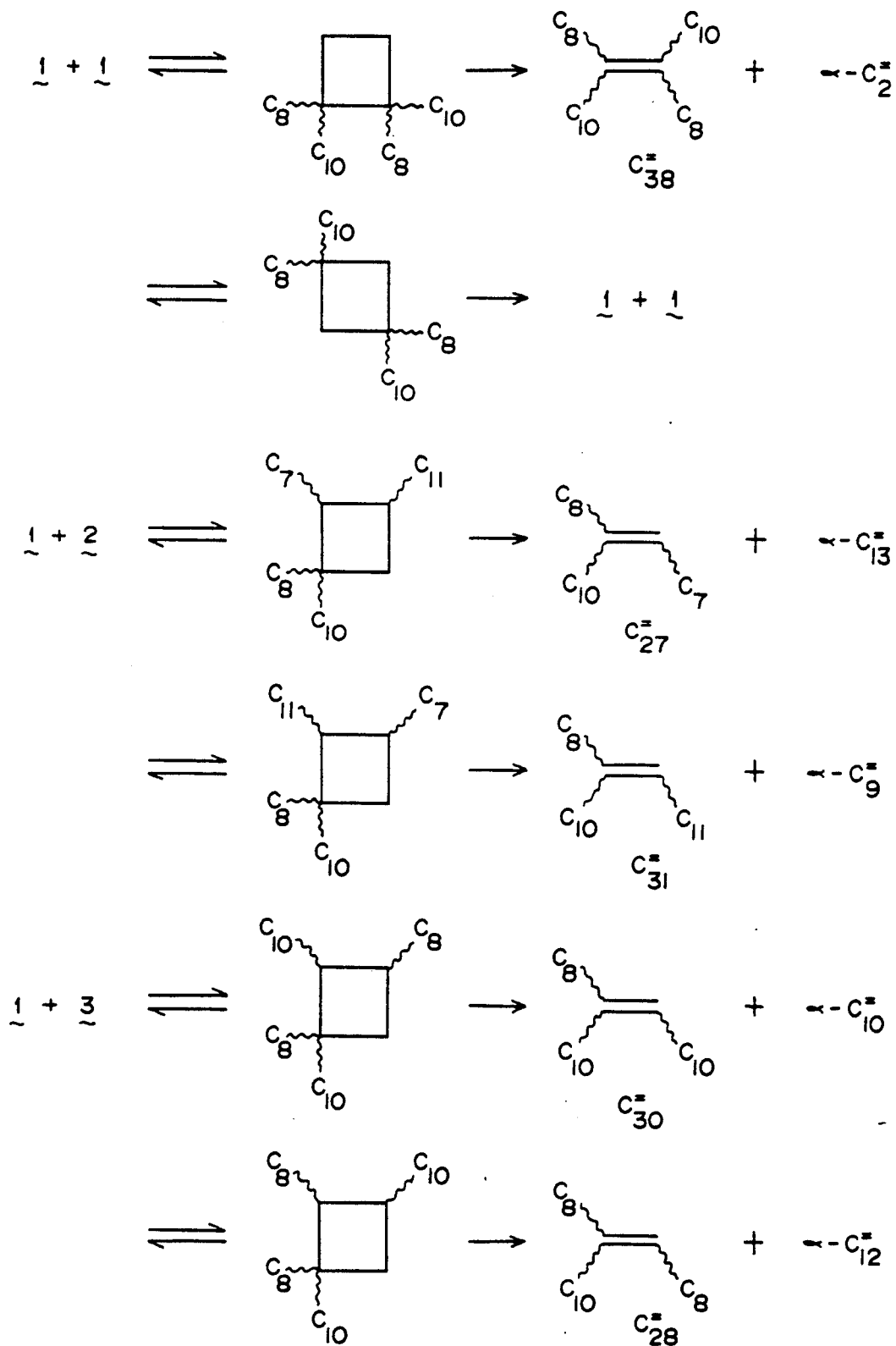
FIG. 2 illustrates the primary reaction pathways in the disproportionation reaction for 1-decene dimers according to the present invention.

The process employed in the present invention to convert alpha-olefin dimers to lube grade mono-olefins is disproportionation, also known as metathesis. Disproportionation is a reaction well-known to those skilled in the organic chemistry arts. Generally, disproportionation is a bimolecular conversion process and is defined as a chemical reaction involving two molecules of the same substance in which one molecule is reduced and the other oxidized, or in which one group is added to one molecule and taken away from another. In the preferred embodiments of the present invention the disproportionation involves two molecules, or moles, of alpha-olefin dimer. The disproportionation of olefins results from cycloaddition of olefins to form cyclobutane derivatives followed by cycloreversion to give back a pair of olefins. The lube product produced in the preferred embodiment herein is essentially a bimolecular adduct of alpha-olefin dimer, accompanied by the splitting off of a smaller olefin molecule to give the same or equal number of moles as the moles of starting dimer. The composition of the product is dependent on the structure of the starting olefinic dimer. With non-symmetrical olefins, exo-methylene olefins such as vinylidenes, or mixtures of olefins the reaction can give other product olefins of higher and lower molecular weight. The reaction is illustrated in FIG. 2 for the three most prevalent $C_{20}$ olefins comprising the HVI-PAO dimers. The upper limit of product molecular size is from combination of the two largest exo-methylene components minus ethylene. The top reaction in FIG. 2 demonstrates this theoretical limit-the formation of tetra-substituted $C_{38}$ olefin from dimer 1. In general, the theoretical upper limit for the compositions of this invention can be expresses as $2n-2$, where n is the number of carbon atoms in the dimer. Basically, the lubricant composition comprises the mono-olefinic bimolecular adduct of $C_{12}$–$C_{40}$ mono-olefin dimer derived from the oligomerization of $C_6$–$C_{20}$ alpha-olefins by the HVI-PAO process. The adduct or lubricant product contains between $2n-2$ and $2n-(n/2+3)$ carbon atoms, where n is the number of carbon atoms in said $C_{12}$–$C_{40}$ mono-olefin or dimer.

Only combinations of the exo-olefin with itself and with the internal olefins produce lube range molecular weight products in the primary reaction pathways. The conversion of the dimers to lube range products is limited by the amount of exo-olefin in the dimer mixture.

The disproportionation reaction process of the present invention can be carried out in any suitable reactor, such as fixed bed, moving bed, stirred tank or slurry reactor. The reaction condition can be temperature between 0°–600° C., but preferably about 300° C. Reaction pressure can be atmospheric to 1000 psig.

The disproportionation catalyst of the present invention can be taken from Group six metal of the Periodic Table of the Elements (reference- Handbook of Chemistry and Physics (Weast) 68th Edition). However, it has been discovered that tungsten oxide is the preferred catalyst, while chromium oxide does not work effectively for the preferred embodiment. The tungsten oxide is dissolved in aqueous ammonia and a porous support such as silica is added. The impregnated silica is dried and then calcined at a temperature between 200° and 900° C. in contact with an oxidizing gas such as air. The catalyst is then reduced at a temperature between 200° and 900° C. with a reducing gas such as carbon monoxide. Other suitable reducing agents include $H_2$, $NH_3$, $H_2S$, and $CS_2$. The catalyst is used in a feed to catalyst ratio between 1:1 and 100:1, but preferably about 50:1.

The following examples of the instant invention are presented merely for illustration purposes and are not intended to limit the scope of the present invention.

EXAMPLE 1

Catalyst Preparation and Activation Procedure

Tungsten oxide ($WO_3$, 13.5 g) is dissolved in dilute ammonium hydroxide. To this solution is added 100 g of silica (Davidson Grade 644). The impregnated silica is dried on a rotary evaporator. It is then calcined in a fluidized bed at 540° C. for 16 hrs. with air, followed by reduction at this temperature with CO for 0.5 hrs. The catalyst is cooled in nitrogen and stored in an inert atmosphere. The catalyst has the deep blue appearance of Tungsten Blue.

EXAMPLE 2

Disproportionation/Metathesis Reaction

In a 100ml flask the catalyst of Example 1 and 1-decene HVI-PAO dimer prepared as described hereinafter is heated in a nitrogen atmosphere at 300° C. The feed to catalyst ratio is 50:1 and the reaction time is 1 hour. Upon distillation, of lighter products and unreacted dimers, a 36% yield is recovered of a fluid having a 688° F. initial boiling point (GC simulated distillation) and the following properties:

cS@40° C.=32 18 cS@100° C.=6.07 VI=138

In the preparation of HVI-PAO dimers, olefins suitable for use as starting material in the preparation of olefinic HVI-PAO oligomers and the by-product dimer used as starting material in the present invention include those olefins containing from 6 to about 20 carbon atoms such as 1-hexene, 1-octene, 1-decene, 1-dodecene and 1-tetradecene and branched chain isomers such as 4-methyl-1-pentene. A preferred 1alkene is 1-decene. Also suitable for use are olefin-containing refinery feedstocks or effluents. Unsaturated HVI-PAO alpha-olefin oligomers are prepared by oligomerization reactions in which a major proportion of the double bonds of the alpha-olefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstroms are preferred.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, CS2, $CH_3SCH_3$, $CH_3SSCH_3$, metal alkyl containing compounds such as $R_3Al$, $R_3B, R_2Mg$, RLi, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. However, oligomerization temperature is preferably between 90°–250° C. at a feedstock to catalyst weight ratio between 10:1 and 30:1. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250° to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have a very wide range of viscosities with high viscosity indices suitable for high performance lubrication use. The product oligomers also have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices. These low branch oligomers maintain better or comparable pour points.

The branch ratios defined as the ratios of $CH_3$ groups to $CH_2$ groups in the reaction products and by-products are calculated from the weight fractions of methyl groups obtained by infrared methods, published in *Analytical Chemistry*. Vol. 25, No. 10, p. 1466 (1953).

$$\text{Branch ratio} = \frac{\text{wt fraction of methyl group}}{1 - (\text{wt fraction of methyl group})}$$

The following examples are presented to illustrate the oligomerization reaction and lubricant grade oligomers produced therefrom. The reaction provides as a by-product the olefinic dimer used as alkylating agent in the present invention. The dimer is separated by distillation from the oligomerization reaction mixture.

EXAMPLE 3

Catalyst Preparation and Activation Procedure 1.9 grams of chromium (II) acetate ($Cr_2(OCOCH_3)_4 2H_2O$) (5.58 mmole) (commercially obtained) is dissolved in 50 cc of hot acetic acid. Then 50 grams of a silica gel of 8-12 mesh size, a surface area of 300 m$^2$/g, and a pore volume of 1 cc/g, also is added. Most of the solution is absorbed by the silica gel. The final mixture is mixed for half an hour on a rotavap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 4

The catalyst prepared in Example 3 (3.2 g) is packed in a 3/8" stainless steel tubular reactor inside an $N_2$ blanketed dry box. The reactor under $N_2$ atmosphere is then heated to 150° C. by a single-zone Lindberg furnace. Prepurified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

EXAMPLE 5

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hrs. | 3.5 | 4.5 | 6.5 | 22.5 |
| Lube Yield, % | 73 | 64 | 59 | 21 |
| Viscosity cS, at | | | | |
| 40° C. | 2548 | 2429 | 3315 | 9031 |
| 100° C. | 102 | 151 | 197 | 437 |
| VI | 108 | 164 | 174 | 199 |

Since the lubricants prepared by the methods described above contain olefinic unsaturation they are typically hydrogenated to stabilize them for lubricant use. Hydrogenation is accomplished by conventional means well known to those skilled in the art. Typically, hydrogenation is carried out with hydrogen and in contact with a hydrogenation catalyst, such as nickel. However, very high molecular weight oligomers may not need to be hydrogenated since the number of olefin bonds in such oligomers is comparatively small.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A process for the preparation of low viscosity lubricant range hydrocarbons having high viscosity index, comprising: contacting olefinic dimer, or mixtures thereof, with a tungsten oxide disproportionation catalyst on a solid support under disproportionation reaction conditions, said dimer comprising the product of the oligomerization of $C_6$-$C_{20}$ alpha-olefins in contact with reduced chromium oxide catalyst on silica support, wherein said disproportionation catalyst has been treated by oxidation at a temperature between 200° C. and 900° C. in the presence of an oxidizing gas and then by treatment with a reducing agent at a temperature and a time sufficient to reduce said catalyst and; separating said disproportionation reaction effluent and recovering said lubricant range hydrocarbons having a viscosity between 3 and 10 cS at 100° C. with a viscosity index greater than 100.

2. The process of claim 1 further comprising hydrogenating said lubricant range hydrocarbons to provide saturated hydrocarbons.

3. The process of claim 1 wherein said metal oxide comprises tungsten oxide and said solid support comprises silica.

4. The process of claim 1 wherein said disproportionation reaction conditions comprise temperature between 0° C. and 600° C. and a feed to catalyst ratio between 1:1 and 100:1.

5. The process of claim 4 wherein said conditions are about 300° C. and 50:1 feed to catalyst ratio.

6. The process of claim 1 wherein said reducing agent comprises carbon monoxide and said oxidizing agent comprises air.

7. The process of claim 1 wherein said alpha-olefins comprise 1-decene and said dimer comprises $C_{20}$ dimer.

8. The process of claim 1 wherein said lubricant range hydrocarbons comprise the mono-olefinic bimolecular adduct of said olefinic dimer, said adduct containing up to 2n−2 carbon atoms, where n is the number of carbon atoms in said dimer.

9. The process of claim 7 wherein said lubricant has a viscosity of about 6 cS at 100° C. with a viscosity index of about 138.

* * * * *